(12) United States Patent
Clubb et al.

(10) Patent No.: US 10,766,923 B2
(45) Date of Patent: Sep. 8, 2020

(54) METHODS AND COMPOSITIONS TO INCREASE THE RATE OF LIGATION REACTIONS CATALYZED BY A SORTASE

(71) Applicant: The Regents of the University of California, Oakland, CA (US)

(72) Inventors: Robert T. Clubb, Culver City, CA (US); Brendan R. Amer, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 25 days.

(21) Appl. No.: 16/072,155

(22) PCT Filed: Jan. 26, 2017

(86) PCT No.: PCT/US2017/015164
§ 371 (c)(1),
(2) Date: Jul. 23, 2018

(87) PCT Pub. No.: WO2017/132395
PCT Pub. Date: Aug. 3, 2017

(65) Prior Publication Data
US 2019/0077829 A1 Mar. 14, 2019

Related U.S. Application Data

(60) Provisional application No. 62/287,364, filed on Jan. 26, 2016.

(51) Int. Cl.
| | |
|---|---|
| *C07K 1/13* | (2006.01) |
| *C07K 7/06* | (2006.01) |
| *C12N 9/52* | (2006.01) |
| *C07K 14/35* | (2006.01) |
| *C07K 14/47* | (2006.01) |
| *C12N 15/113* | (2010.01) |
| *C12N 15/52* | (2006.01) |
| *C12N 15/63* | (2006.01) |

(52) U.S. Cl.
CPC ............ *C07K 1/13* (2013.01); *C07K 7/06* (2013.01); *C07K 14/35* (2013.01); *C07K 14/47* (2013.01); *C12N 9/52* (2013.01); *C12N 15/113* (2013.01); *C12N 15/52* (2013.01); *C12N 15/63* (2013.01); *C12Y 304/2207* (2013.01); *C07K 2319/00* (2013.01); *C07K 2319/21* (2013.01); *C07K 2319/35* (2013.01); *C07K 2319/50* (2013.01); *C07K 2319/90* (2013.01); *C12N 2310/3181* (2013.01); *C12N 2310/3517* (2013.01)

(58) Field of Classification Search
None
See application file for complete search history.

(56) References Cited

U.S. PATENT DOCUMENTS 9,588,110 B2* 3/2017 Huynh .................. C12N 9/52

FOREIGN PATENT DOCUMENTS

| | | |
|---|---|---|
| EP | 2391714 A2 | 12/2011 |
| WO | WO 2005/051976 A2 | 6/2005 |
| WO | WO 2010/087994 A2 | 8/2010 |
| WO | WO 2011/056911 A2 | 5/2011 |
| WO | WO 2014/145441 A1 | 9/2014 |
| WO | WO 2017/132395 A1 | 8/2017 |

OTHER PUBLICATIONS

PCT International Search Report and Written Opinion dated May 1, 2017 issued in PCT/US2017/015164.
PCT International Preliminary Report on Patentability and Written Opinion dated Jul. 31, 2018 issued in PCT/US2017/015164.
Amer et al. (Feb. 2016) "Rapid addition of unlabeled silent solubility tags to proteins using a new substrate-fused sortase reagent" *J Biomol NMR* 64:197-205 DOI 10.1007/s10858-016-0019-z [9 pages].
Antos et al. (2008) "Lipid Modification of Proteins through Sortase-Catalyzed Transpeptidation" *J. Am. Chem. Soc.* 130: 16338-16343.
Chan et al. (Nov. 2007) "Covalent Attachment of Proteins to Solid Supports and Surfaces via Sortase-Mediated Ligation" *PLoS ONE* 11: e1164 doi:10.1371/journal.pone.0001164 [5 pages].
Freiburger et al. (2015) "Efficient segmental isotope labeling of multi-domain proteins using Sortase A." *J. Biomol. NMR*, 63: 1-8.
Kobashigawa et al. (2009) "Attachment of an NMR-invisible solubility enhancement tag using a sortase-mediated protein ligation method" *J. Biomol. NMR*, 43: 145-150.
Levary et al. (Apr. 2011) "Protein-Protein Fusion Catalyzed by Sortase A" *PLoS ONE* 6(4): e18342 doi:10.1371/journal.pone.0018342 [6 pages].
Mazmanian et al. (1999) "*Staphylococcus aureus* Sortase, an Enzyme that Anchors Surface Proteins to the Cell Wall" *Science* (80)285: 760-763.
Parthasarathy et al. (2007) "Sortase A as a novel molecular "stapler" for sequence-specific protein conjugation." *Bioconjug. Chem.* 18: 469-476.

(Continued)

*Primary Examiner* — Kagnew H Gebreyesus
(74) *Attorney, Agent, or Firm* — Tom Hunter; Weaver Austin Villeneuve & Sampson LLP

(57) ABSTRACT

In various embodiments methods and compositions to increase the rate and/or activity of ligation reactions catalyzed by a sortase. In certain embodiments reagents are provided that comprises, inter alia, a polypeptide comprising an amino terminal polyglycine sequence comprising at least three contiguous Gly residues (e.g., a triglycine sequence, a tetraglycine sequence, a pentaglycine sequence, etc.) followed by a peptide that is to be ligated to a moiety followed by a sequence comprising the catalytic domain of a Sortase A enzyme.

17 Claims, 4 Drawing Sheets

Specification includes a Sequence Listing.

(56) References Cited

OTHER PUBLICATIONS

Pritz et al. (2007) "Synthesis of biologically active peptide nucleic acid-peptide conjugates by sortase-mediated ligation." *J. Org. Chem.* 72: 3909-3912.

Refaei et al. (2011) "Observing selected domains in multi-domain proteins via sortase-mediated ligation and NMR spectroscopy." *J. Biomol. NMR*, 49: 3-7 [NIH Public Access—Author Manuscript—9 pages].

Sakamoto et al. (2010) "Enzyme-mediated site-specific antibody-protein modification using a ZZ domain as a linker." *Bioconjug. Chem.* 21: 2227-2233.

Spirig et al. (2011) "Sortase enzymes in Gram-positive bacteria." *Mol. Microbiol.* 82: 1044-1059.

Weber et al. (Jul. 2014) "Versatile Recombinant SUMOylation System for the Production of SUMO-Modified Protein" *PLoS ONE* 9(7): e102157 doi:10.1371/journal.pone.0102157 [12 pages].

\* cited by examiner

METHODS AND COMPOSITIONS TO INCREASE THE RATE OF LIGATION REACTIONS CATALYZED BY A SORTASE

CROSS-REFERENCE TO RELATED APPLICATIONS

This application is a U.S. 371 National Phase of PCT/US2017/015164, filed on Jan. 26, 2017, which claims priority to and benefit of U.S. Ser. No. 62/287,364, filed on Jan. 26, 2016, both of which are incorporated herein by reference in their entirety for all purposes.

STATEMENT OF GOVERNMENTAL SUPPORT

This invention was made with government support under Grant No. AI52217 awarded by the National Institutes of Health, and under Grant No: DE-FC02-02ER63421 awarded by the US Department of Energy Office of Science, Office of Biological and Environmental Research program. The Government has certain rights in this invention.

INCORPORATION BY REFERENCE OF SEQUENCE LISTING PROVIDED AS A TEXT FILE

A Sequence Listing is provided herewith as a text file, "UCLA-P157US_ST25.txt" created on Dec. 31, 2019 and having a size of 4.89 kb. The contents of the text file are incorporated by reference herein in their entirety

BACKGROUND

The sortase A (SrtA) enzyme from *Staphylococcus aureus* is widely used as a tool to catalyze in vitro ligation reactions that join biomolecules. It is arguably the most effective tool for this purpose. It functions as a transpeptidase that joins two peptides, a peptide containing the sequence LPXTG (SEQ ID NO:2) (where X can be any amino acid) and a peptide containing a polyglycine (e.g., penta-glycine (Gly$_5$, SEQ ID NO:1)) at its N-terminus. The latter peptide can contain as few as three glycine residues. In the reaction, SrtA joins the peptides by cleaving the LPXTG (SEQ ID NO:2) motif between threonine and glycine and subsequently joins the carboxyl group of threonine to the amino group of penta-glycine (Mazmanian (1999) *Science*, 285:760-763; Spirig et al. (2011) *Mol. Microbiol.* 82:1044-1059). As a result the original substrates are joined via peptide bond.

SrtA transpeptidation reaction has been used for generating antibody conjugates, generating nucleic acid-protein fusions, PEGylating and/or lipidating proteins, in live cell-labeling, in protein cyclization, in silent labeling, in domain labeling, and to add proteins to solid supports (see, e.g., Parthasarathy et al. (2007) *Bioconjug. Chem.* 18: 469-476; Chan et al. (2007) *PLoS One*, 2: e1164. doi:10.1371; Pritz et al. (2007) *J. Org. Chem.* 72: 3909-3912; Antos et al. (2008) *J. Am. Chem. Soc.* 130: 16338-16343; Kobashigawa et al. (2009) *J. Biomol. NMR*, 43: 145-150; Sakamoto et al. (2010) *Bioconjug. Chem.* 21: 2227-2233; Levary et al. (2011) *PLoS One*, 6: e18342; Refaei et al. (2011) *J. Biomol. NMR*, 49: 3-7; Freiburger et al. (2015) *J. Biomol. NMR*, 63: 1-8).

SUMMARY

It is believed that previously, all SrtA modifications make use of three reagent reaction: the isolated SrtA enzyme and two substrates (a substrate containing a GGGGG (SEQ ID NO:1), or in some instances only three glycine residues sequence and a substrate containing an LPXTG (SEQ ID NO:2) motif).

A novel ligation system is provided herein that, in various embodiments, provides a polyglycine sequence comprising at least three contiguous Gly residues (e.g., a triglyicine (GGG), a tetraglycine (GGGG, (SEQ ID NO:3)), a penta-glycine (GGGGG (SEQ ID NO:1), etc.) attached to a sortase enzyme (e.g., SrtA). It was a surprising discovery that attachment of the polyglycine (e.g., GGGGG SEQ ID NO:1) substrate to the sortase significantly increased the sortase reaction rate rather than blocking or inhibiting access to the activate site of the sortase. It is believed that use of sortases modified as described herein can significantly improve sortase (e.g., SrtA) mediated ligation reactions. Such reactions include but are not limited to the generation of antibody conjugates, the generation of nucleic acid-protein fusions, protein PEGylation, protein lipidation, live cell labeling, protein cyclization, silent labeling, domain labeling, and addition of proteins to solid supports.

Various embodiments contemplated herein may include, but need not be limited to, one or more of the following:

Embodiment 1

A reagent for ligating a desired polypeptide to a target moiety having a linking peptide attached thereto consisting or comprising a LPXTG (SEQ ID NO:2) amino acid motif in the carboxyl terminal, said reagent comprising:
a polypeptide comprising an amino terminal polyglycine sequence comprising at least three contiguous Gly residues sequence followed by said desired polypeptide sequence followed by a sequence comprising the catalytic domain of a Sortase A enzyme.

Embodiment 2

The reagent of embodiment 1, wherein said polyglycine sequence comprises or consists of at least four contiguous Gly residues.

Embodiment 3

The reagent of embodiment 1, wherein said polyglycine sequence comprises or consists of at least five contiguous Gly residues.

Embodiment 4

The reagent of embodiment 1, wherein said polyglycine sequence comprises at least 6, or at least 7, or at least 8, or at least 9, or at least 10 contiguous Gly residues up to about 50 contiguous Gly residues, or up to about contiguous 40 Gly residues or up to about contiguous 30 Gly residues, or up to about contiguous 20 Gly residues, or up to about 15 contiguous Gly residues, or about 6 contiguous Gly residues, or about contiguous 7 Gly residues, or at about 8 contiguous Gly residues, or about 9 contiguous Gly residues, or about 10 contiguous Gly residues.

Embodiment 5

The reagent according to any one of embodiments 1-4, wherein said reagent catalyzes a transpeptidation reaction substantially more rapidly and/or substantially more completely than a transpeptidation reaction performed using a sortase without an attached amino terminal pentaglycine.

Embodiment 6

The reagent according to any one of embodiments 1-5, wherein a protease cleavage site is disposed between said desired polypeptide and said Sortase A enzyme.

Embodiment 7

The reagent of embodiment 6, wherein said protease cleavage site comprises a protease site recognized by a protease selected from the group consisting of a serine protease, a cysteine or cysteine-like protease, and a metalloprotease.

Embodiment 8

The reagent of embodiment 6, wherein said protease cleavage site comprises a protease site recognized by Ulp-1.

Embodiment 9

The reagent according to any one of embodiments 1-8, wherein said reagent further comprises a carboxyl terminal affinity tag.

Embodiment 10

The reagent of embodiment 9, wherein said affinity tag comprises a poly histidine tag.

Embodiment 11

The reagent of embodiment 9, wherein said affinity tag comprises a $His_6$ (SEQ ID NO:4) tag.

Embodiment 12

The reagent according to any one of embodiments 1-11, wherein said catalytic domain of a sortase A enzyme comprise a catalytic domain of a *Staphylococcus aureus* sortase A enzyme.

Embodiment 13

The method according to any one of embodiments 1-12, wherein said wherein said desired protein ranges in length from about 5 up to about 200 amino acids, or from about 10 up to about 100 amino acids, or up to about 75 amino acids, or up to about 50 amino acids, or up to about 40 amino acids, or up to about 30 amino acids, or up to about 20 amino acids, or up to about 15 amino acids.

Embodiment 14

The reagent according to any one of embodiments 1-13, wherein said desired protein comprises SUMO.

Embodiment 15

A method of attaching a desired polypeptide to a moiety, said method comprising:
providing said moiety with a linking peptide attached thereto consisting or comprising a LPXTG (SEQ ID NO:2) amino acid motif in the carboxyl terminal; and
contacting said moiety with a reagent according to any one of embodiments 1-13 whereby the sortase comprising said reagent catalyzes a transpeptidation attaching the moiety to the desired polypeptide via said LPXTG (SEQ ID NO:2) motif.

Embodiment 16

The method of embodiment 15, wherein said linking peptide comprises or consists of an amino acid sequence selected from the group consisting of LPETG (SEQ ID NO:18), LPATG (SEQ ID NO:19), LPKTG (SEQ ID NO:20), LPTTG (SEQ ID NO:21), LPSTG (SEQ ID NO:22), LPLTG (SEQ ID NO:23), and LPYTG (SEQ ID NO:24).

Embodiment 17

The method of embodiment 15, wherein said target peptide comprises or consists of the amino acid sequence LPETG (SEQ ID NO:18).

Embodiment 17

The method of embodiment 15, wherein said target peptide comprises or consists of the amino acid sequence LPETG (SEQ ID NO:22).

Embodiment 18

The method according to any one of embodiments 15-17, wherein said reagent comprises a carboxyl terminal affinity tag and the method comprises affinity purification of the moiety with the attached desired polypeptide.

Embodiment 19

The method of embodiment 18, wherein said affinity tag comprises a poly histidine tag and said affinity purification comprises contacting with an affinity resin containing bound bivalent nickel or cobalt ion.

Embodiment 20

The method according to any one of embodiments 15-19, wherein a protease recognition site is disposed between said desired polypeptide and said sortase and said method comprises contacting the moiety with the attached desired polypeptide with a protease that recognizes and cleaves at said site thereby removing the sortase from the attached desired polypeptide.

Embodiment 21

The method of embodiment 20, wherein said protease is selected from the group consisting of group consisting of a serine protease, a cysteine or cysteine-like protease, and a metalloprotease.

Embodiment 22

The method of embodiment 20, wherein said protease is Ulp-1.

Embodiment 23

The method according to any one of embodiments 20-21, wherein said protease is attached to an affinity tag.

Embodiment 24

The method according to any one of embodiments 15-23, wherein said moiety comprises a moiety selected from the group consisting of a polypeptide, a nucleic acid, an antibody, a lectin, a sugar, a small organic molecule, a lipid, an a solid support.

Embodiment 25

The method of embodiment 24, wherein said moiety comprises a polypeptide.

Embodiment 26

The method of embodiment 25, wherein said target peptide is expressed as a fusion with said polypeptide.

Embodiment 27

The method of embodiment 24, wherein said moiety comprises an antibody.

Embodiment 28

The method of embodiment 27, wherein said target peptide is expressed as a fusion with a chain comprising said antibody or is chemically conjugated to said antibody.

Embodiment 29

The method of embodiment 24, wherein said moiety comprises a nucleic acid, a lectin, a sugar, or a small organic molecule and said target peptide is chemically conjugated to said nucleic acid, lectin, sugar, or small organic molecule.

Embodiment 30

The method of embodiment 24, wherein said moiety comprises a solid support.

Embodiment 31

The method of embodiment 30, wherein said solid support comprises a surface of a well or vessel, a bead, or a channel in a microfluidic device.

Embodiment 32

The method of embodiment 30, wherein said solid support comprises a solid support comprises a surface of a BiaCore.

Embodiment 33

A reagent for tagging by SUMO, said reagent comprising a polypeptide comprising an amino terminal polyglycine sequence comprising at least three contiguous Gly residues followed by a SUMO polypeptide followed by a sequence comprising the catalytic domain of a Sortase A enzyme.

Embodiment 34

The reagent of embodiment 33, wherein said polyglycine sequence comprises or consists of at least four contiguous Gly residues.

Embodiment 35

The reagent of embodiment 33, wherein said polyglycine sequence comprises or consists of at least five contiguous Gly residues.

Embodiment 36

The reagent of embodiment 33, wherein said polyglycine sequence comprises at least 6, or at least 7, or at least 8, or at least 9, or at least 10 contiguous Gly residues up to about 50 contiguous Gly residues, or up to about contiguous 40 Gly residues or up to about contiguous 30 Gly residues, or up to about contiguous 20 Gly residues, or up to about 15 contiguous Gly residues, or about 6 contiguous Gly residues, or about contiguous 7 Gly residues, or at about 8 contiguous Gly residues, or about 9 contiguous Gly residues, or about 10 contiguous Gly residues.

Embodiment 37

The reagent of embodiments 33-36, wherein said reagent comprises an affinity tag attached to the carboxyl terminus.

Embodiment 38

The reagent of embodiment 37, wherein said affinity tag comprises a polyhistidine.

Embodiment 39

The reagent of embodiment 38, wherein said affinity tag comprises or consists of $His_6$ (SEQ ID NO:4).

Embodiment 40

The reagent according to any one of embodiments 33-39, wherein said catalytic domain of a sortase A enzyme comprise a catalytic domain of a *Staphylococcus aureus* sortase A enzyme.

Embodiment 41

The reagent according to any one of embodiments 33-40, wherein said catalyzes a transpeptidation reaction substantially more rapidly and/or substantially more completely than a transpeptidation reaction performed using a sortase without an attached amino terminal pentaglycine.

Embodiment 42

A method of silent tagging of a target protein with SUMO, said method comprising:
  providing said target protein attached to a linking peptide consisting or comprising a LPXTG (SEQ ID NO:2) amino acid motif in the carboxyl terminal; and
  contacting said target protein with a reagent comprising SUMO according to any one of embodiments 33-41, where said sortase catalyzes a transpeptidase reaction attaching said reagent comprising SUMO to said target protein.

Embodiment 43

The method of embodiment 42, further comprising contacting said target protein with the attached reagent with a Ulp1 protease to cleave the sortase from said attached reagent.

Embodiment 44

The method according to any one of embodiments 42-43, wherein Said linking peptide comprises or consists of a sequence selected from the group consisting of LPETG (SEQ ID NO:18), LPATG (SEQ ID NO:19), LPKTG (SEQ ID NO:20), LPTTG (SEQ ID NO:21), LPSTG (SEQ ID NO:22), LPLTG (SEQ ID NO:23), and LPYTG (SEQ ID NO:24).

Embodiment 45

The method according to any one of embodiments 42-43, wherein Said linking peptide comprises or consists of the amino acid sequence LPETG (SEQ ID NO:18).

Embodiment 46

The method according to any one of embodiments 42-45, wherein said target protein attached to a linking peptide further comprise a SUMO polypeptide on the amino terminus of said target protein.

Embodiment 47

The method according to any one of embodiments 42-46 wherein said target protein attached to a linking peptide comprises an amino terminus affinity tag present on the amino terminus of the target protein, or on the amino terminus of a SUMO when said amino terminal SUMO is present.

Embodiment 48

The method of embodiment 47, wherein said affinity tag comprises a polyhistidine.

Embodiment 49

The method of embodiment 48, wherein said affinity tag comprises or consists of $His_6$ (SEQ ID NO:4).

Embodiment 50

A vector for preparing a reagent for ligating a desired polypeptide to a moiety, said vector comprising a promotor operably linked to a nucleic acid sequence encoding a polyglycine sequence comprising at least three contiguous Gly residues, followed by a cloning site, following by a nucleic acid sequence encoding an amino acid sequence comprising the catalytic domain of a sortase.

Embodiment 51

The vector of embodiment 50, wherein said polyglycine sequence comprises or consists of at least four contiguous Gly residues.

Embodiment 52

The vector of embodiment 50, wherein said polyglycine sequence comprises or consists of at least five contiguous Gly residues.

Embodiment 53

The vector of embodiment 50, wherein said polyglycine sequence comprises at least 6, or at least 7, or at least 8, or at least 9, or at least 10 contiguous Gly residues up to about 50 contiguous Gly residues, or up to about contiguous 40 Gly residues or up to about contiguous 30 Gly residues, or up to about contiguous 20 Gly residues, or up to about 15 contiguous Gly residues, or about 6 contiguous Gly residues, or about contiguous 7 Gly residues, or at about 8 contiguous Gly residues, or about 9 contiguous Gly residues, or about 10 contiguous Gly residues.

Embodiment 54

The vector according to any one of embodiments 50-53, wherein said vector comprises a nucleic acid encoding a protease recognition site between said cloning site and said sortase.

Embodiment 55

The vector of embodiment 54, wherein said protease recognition site comprises a protease site recognized by a protease selected from the group consisting of a serine protease, a cysteine or cysteine-like protease, and a metalloprotease.

Embodiment 56

The vector of embodiment 54, wherein said protease cleavage site comprises a protease site recognized by Ulp-1.

Embodiment 57

The vector according to any one of embodiments 50-56, wherein said vector further encodes a carboxyl terminal affinity tag.

Embodiment 58

The vector of embodiment 57, wherein said affinity tag comprises a poly histidine tag.

Embodiment 59

The vector of embodiment 57, wherein said affinity tag comprises a $His_6$ (SEQ ID NO:4) tag.

Embodiment 60

The vector according to any one of embodiments 50-59, wherein said catalytic domain of a sortase A enzyme comprise a catalytic domain of a *Staphylococcus aureus* sortase A enzyme.

Embodiment 61

The vector according to any one of embodiments 50-60, wherein said cloning site is a multiple cloning site.

Embodiment 62

The vector according to any one of embodiments 50-61, wherein said promoter is an inducible promoter.

Embodiment 63

The vector according to any one of embodiments 50-61, wherein said promoter is a constitutive promoter.

Embodiment 64

A vector for preparing a target protein for silent tagging by a SUMO-sortase reagent, said vector comprising a promotor operably linked to a cloning site followed by a nucleic acid sequence encoding a linking peptide consisting or comprising a LPXTG (SEQ ID NO:2) amino acid motif.

Embodiment 65

The vector of embodiment 64, wherein said linking peptide comprises or consists of a sequence selected from the group consisting of LPETG (SEQ ID NO:182), LPATG (SEQ ID NO:19), LPKTG (SEQ ID NO:20), LPTTG (SEQ ID NO:21), LPSTG (SEQ ID NO:22), LPLTG (SEQ ID NO:23), and LPYTG (SEQ ID NO:24).

Embodiment 66

The vector of embodiment 64, wherein said linking peptide comprises or consists of the amino acid sequence LPETG (SEQ ID NO:18).

Embodiment 67

The vector according to any one of embodiments 64-66, wherein said vector encodes a SUMO attached to the amino terminus of a target protein encoded by a nucleic acid sequence inserted into said cloning site.

Embodiment 68

The vector according to any one of embodiments 64-67, wherein said vector encodes an amino terminal affinity tag.

Embodiment 69

The vector of embodiment 68, wherein said affinity tag comprises a poly histidine tag.

Embodiment 70

The vector of embodiment 68, wherein said affinity tag comprises a $His_6$ (SEQ ID NO:4) tag.

Embodiment 71

The vector according to any one of embodiments 64-70, wherein said cloning site is a multiple cloning site.

Embodiment 72

The vector according to any one of embodiments 64-71, wherein said promoter is an inducible promoter.

Embodiment 73

The vector according to any one of embodiments 50-71, wherein said promoter is a constitutive promoter.

Embodiment 74

A kit for ligating a desired polypeptide to a target moiety having a linking peptide attached thereto consisting or comprising a LPXTG (SEQ ID NO:2) amino acid motif, said kit comprising: a container containing a first vector according to any one of embodiments 50-63.

Embodiment 75

The kit of embodiment 74, wherein said kit comprises a container containing a second vector comprising a promotor operably linked to a cloning site followed by a nucleic acid sequence encoding a linking peptide consisting or comprising a LPXTG (SEQ ID NO:2) amino acid motif.

Embodiment 76

The kit of embodiment 75, wherein said linking peptide comprises or consists of a sequence selected from the group consisting of LPETG (SEQ ID NO:18), LPATG (SEQ ID NO:19), LPKTG (SEQ ID NO:20), LPTTG (SEQ ID NO:21), LPSTG (SEQ ID NO:22), LPLTG (SEQ ID NO:23), and LPYTG (SEQ ID NO:24).

Embodiment 77

The kit of embodiment 75, wherein said linking peptide comprises or consists of the amino acid sequence LPETG (SEQ ID NO:18).

Embodiment 78

The kit according to any one of embodiments 74-77, wherein said second vector encodes an amino terminal affinity tag.

Embodiment 79

The kit of embodiment 78, wherein said affinity tag comprises a poly histidine tag.

Embodiment 80

The kit of embodiment 78, wherein said affinity tag comprises a $His_6$ (SEQ ID NO:4) tag.

Embodiment 81

The kit according to any one of embodiments 74-80, wherein said cloning site is a multiple cloning site.

Embodiment 82

The vector according to any one of embodiments 74-81, wherein said promoter is an inducible promoter.

Embodiment 83

The vector according to any one of embodiments 74-81, wherein said promoter is a constitutive promoter.

Embodiment 84

A kit for silent tagging using a SUMO-sortase tagging reagent, said kit comprising: a container containing a SUMO-sortase tagging reagent according to any one of embodiments 33-41.

Embodiment 85

The kit of embodiment 84, wherein said kit comprises a container containing a vector for preparing a target protein for silent tagging by a SUMO-sortase reagent according to any one of embodiments 64-73.

Definitions

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The term "polyglycine sequence" refers to a polypeptide or a domain of a polypeptide comprising (or consisting of) at least two contiguous glycine (Gly) residues. In certain embodiments the polyglycine sequence comprises at least three contiguous Gly residues, or at least four contiguous Gly residues, or at least five contiguous Gly residues. In certain embodiments the polyglycine sequence comprises at least 6, or at least 7, or at least 8, or at least 9, or at least 10 Gly residues up to about 50 Gly residues, or up to about 40 Gly residues or up to about 30 Gly residues, or up to about 20 Gly residues, or up to about 15 Gly. In certain embodiments the polyglycine sequence comprises or consists of about 6 contiguous Gly residues, or about 7 contiguous Gly residues, or at about 8 contiguous Gly residues, or about 9 contiguous Gly residues, or about contiguous 10 Gly residues.

The term small organic molecules refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The terms "epitope tag" or "affinity tag" are used interchangeably herein, and used refers to a molecule or domain of a molecule that is specifically recognized by an antibody or other binding partner. The term also refers to the binding partner complex as well. Thus, for example, biotin or a biotin/avidin complex are both regarded as affinity tag(s). In addition to epitopes recognized in epitope/antibody interactions, affinity tags also comprise "epitopes" recognized by other binding molecules (e.g., ligands bound by receptors), ligands bound by other ligands to form heterodimers or homodimers, polyhistidine (e.g., His$_6$ (SEQ ID NO:4) bound by Ni-NTA, biotin bound by avidin, streptavidin, or anti-biotin antibodies, and the like.

Epitope tags are well known to those of skill in the art. Moreover, antibodies specific to a wide variety of epitope tags are commercially available. These include but are not limited to antibodies against the DYKDDDDK (SEQ ID NO:5) epitope, c-myc antibodies (available from Sigma, St. Louis), the HNK-1 carbohydrate epitope, the HA epitope, the HSV epitope, and the like. In addition, vectors for epitope tagging proteins are commercially available. Thus, for example, the pCMV-Tag1 vector is an epitope tagging vector designed for gene expression in mammalian cells. A target gene inserted into the pCMV-Tag1 vector can be tagged with the FLAG® epitope (N-terminal, C-terminal or internal tagging), the c-myc epitope (C-terminal) or both the FLAG (N-terminal) and c-myc (C-terminal) epitopes.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain antibodies include single chain antibodies (antibodies that exist as a single polypeptide chain), including, but not limited to single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer that can be expressed from a nucleic acid including $V_H$- and $V_L$-encoding sequences either joined directly or joined by a peptide-encoding linker (see, e.g., Huston, et al. (1988) *Proc. Nat. Acad. Sci. USA*, 85: 5879-5883). While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). In certain embodiments, antibodies include all that have been displayed on phage (e.g., scFv, Fv, Fab and disulfide linked Fv (Reiter et al. (1995) *Protein Eng.* 8: 1323-1331).

DETAILED DESCRIPTION

Figure 1:
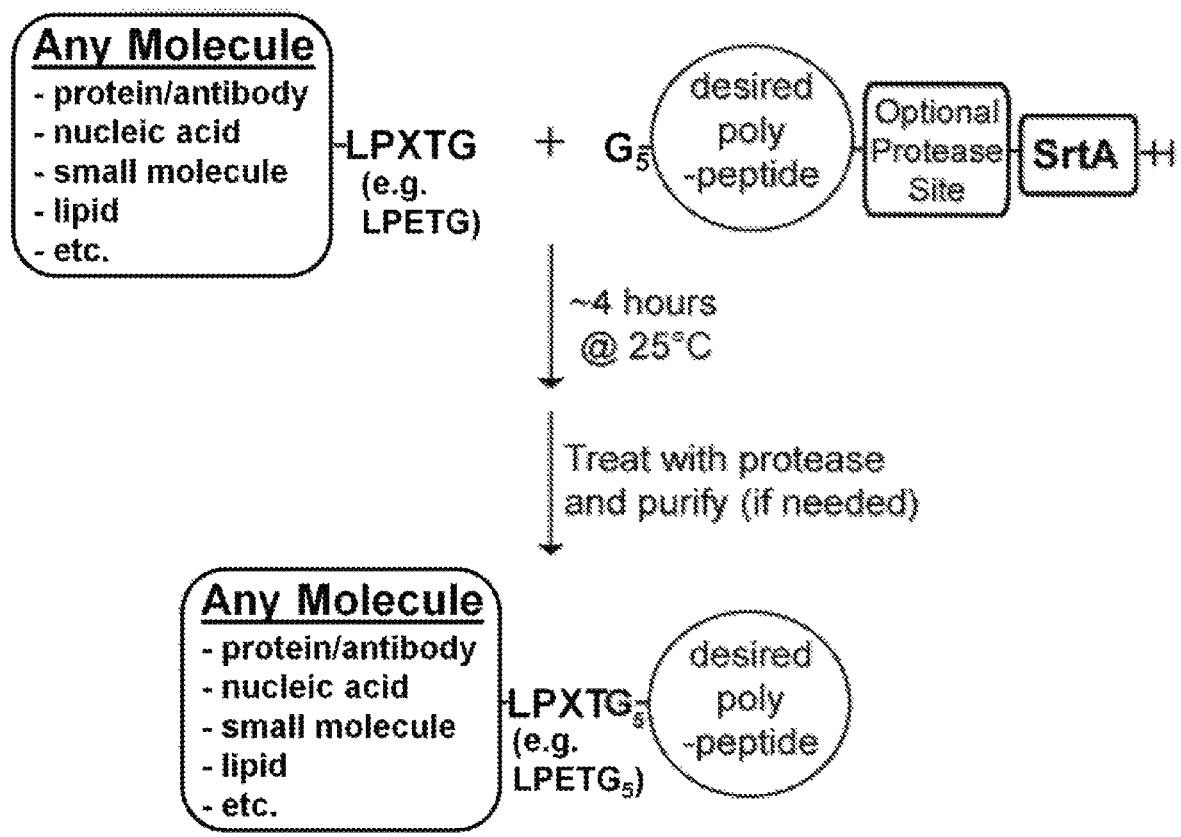
FIG. 1 schematically illustrates one method of ligating polypeptides utilizing a polyglycine- (e.g., a pentaglycine)-modified sortase as described herein.

In various embodiments, compositions, methods, and kits are provided that facilitate and improve sortase mediated ligation reactions in any of a wide number of contexts.

Ligation reactions catalyzed by a sortase (e.g., *Staphylococcus aureus* SrtA) can require several days to reach completion because the enzyme is not very active in vitro. The new technology provided herein significantly increases the rate at which a sortase (e.g., SrtA) ligates biomolecules. This is achieved, inter alia, by fusing the nucleophile substrate a polyglycine (e.g., penta-glycine, tri-glycine, etc.) to the sortase enzyme. In a typical embodiment, a polypeptide is produced that contains a penta-glycine sequence at its N-terminus, which is followed by the sequence that encodes the catalytic domain of SrtA. This substantially increases the effective concentration of the penta-glycine nucleophile near the active site thereby accelerating the rate of transpeptidation. The rate enhancement is achieved because the isolated SrtA enzyme binds the Gly$_5$ (SEQ ID NO:1) nucleophile with weak affinity (Km=140 µM) (see, e.g., Chen et al. 2011). The utility of this approach is demonstrated constructing a reagent that joins the SUMO domain to proteins (see, e.g., Example 1, herein). This is only illustrative application that can benefit using the modified sortase and approach described herein. Fusing nucleophiles that contain as few as 3 glyhcine residues to SrtA should also exhibit elevated reaction kinetics.

Rate Enhancement Demonstration.

By way of illustration, Example 1 describes ligation a SUMO domain to the C-terminus of a protein. As described in Example 1, a SUMO-tagging reagent was constructed that consists of a SUMO-SrtA fusion protein harboring five glycine residues at its N-terminus and a histidine tag at its C-terminus (Gly5-SUMO-SrtA-6×His). The SUMO-tagging reagent attaches SUMO to its target protein ~18 times faster than previously described methods that used the isolated SrtA enzyme.

In this illustrative method, the SUMO-tagging system enables the rapid production of highly concentrated silently SUMO tagged isotopically enriched target protein for characterization by NMR. In our procedure, the isotopically enriched protein is first expressed as a 6×His-SUMOProtein fusion (FIG. 2B). The N-terminal 6×His-SUMO tag is then replaced in a single step with an unlabeled C-terminal SUMO tag, and the resultant silently tagged protein purified in a single step (FIG. 2B). The SUMO-tagging system is based on the SrtA-mediated approach developed by Kobashigawa and colleagues, but simplifies the process by creating a single SUMO-SrtA reagent that silently tags any protein containing the sequence LPXTG (SEQ ID NO:2) at its C-terminus. The procedure makes use of only two reagents, the new silent tagging reagent and purified protein containing a C-terminal LPXTG sequence. When the tagging reagent and fusion protein are incubated with one another, the reagent joins itself via a peptide bond from the C-terminal end of 6×His-SUMO-Protein-LPETG to create a 6×His-SUMO-Protein-LPET-Gly5-SUMO-SrtA-6×His product. The ligation mixture is then incubated with 6×His-Ulp1 protease, releasing the N-terminal SUMO tag (6×His-SUMO), the SrtA enzyme (SrtA-6×His) and the desired silently tagged protein product (Protein-LPET-Gly5-SUMO). Because the product does not contain a histidine tag, it can readily be purified from the other reaction components by affinity purification.

More General Applications:

The approach described herein can be generalized to increase the rate at which a sortase (e.g., SrtA) ligates peptides or polypeptides to molecules or other moieties that contain the sequence LPXTG or that are attached to "linking peptide" comprising the sequence LPXTG. One illustrative approach is shown FIG. 1. The sequence LPXTG (SEQ ID NO:2) is appended to site that will be modified. Previously, among others, LPXTG (SEQ ID NO:2) has been appended to proteins, small molecules, cells, and solid surfaces and methods of attaching the LPXTG (SEQ ID NO:2) (or other linking peptide) to the molecule or moiety are well known to those of skill in the art.

For example, where the reaction is used to attach a first polypeptide to a second polypeptide or to an antibody, the linking peptide (containing the LPXTG motif or other cell sorting signal motif recognized by a sortase) can be expressed as a fusion with the first polypeptide or antibody chain (directly attached or with an intervening peptide linker such as GGGGS (SEQ ID NO:6), (GGGGS)$_3$ (SEQ ID NO:7), and the like). Where the reaction is used to attach a molecule that is not a polypeptide (e.g., a nucleic acid, a lipid, a small organic molecule, a solid support, and the like) the linker peptide can be chemically conjugated to the molecule, solid support, etc.

In the general method schematically illustrated in FIG. 1, a SrtA reagent is constructed to rapidly modify the target site containing the LPXTG (SEQ ID NO:2) sequence. As illustrated, the SrtA reagent contains: (i) the sequence GGGGG (SEQ ID NO:1) at its N-terminus (although different length polyglycine domains can be used), (ii) a peptide or polypeptide sequence that will be ligated to the LPXTG (SEQ ID NO:2) sequence, (iii) an optional amino acid sequence that can be selectively proteolyzed if desired and (iv) the sequence of the SrtA catalytic domain. As demonstrated in Example 1, the sortase (e.g., SrtA) reagent will rapidly ligate itself to the target molecule that contains the sequence LPXTG. If desired, the SrtA enzyme can then be removed by adding the appropriate protease.

Illustrative Applications.

The compositions and methods described herein can increase the rate and extent of modifications catalyzed by the SrtA sortase. There are many potential commercial applications for sortase-mediated ligation that can benefit from this technology. Illustrative applications include, but are not limited to:

1) Generating Nucleic Acid-Protein conjugates. These conjugates can be used to deliver the nucleic acid into the cell so as to modify the genome or modulate gene expression (see, e.g., Pritz et al. (2007) *J. Org. Chem.* 72: 3909-3912);

2) Covalent attachment of proteins and to solid supports and surfaces. This can be used to construct materials for biosensing and biocatalysis (see, e.g., Chan et al. (2007) *PLoS One*, 2: e1164);

3) Lipid modification of proteins through sortase-catalyzed transpeptidation. This allows for the preparation of proteins that can be localized to regions of the cell via attached lipids. E.g. attachment of lipids to Ras and Rab proteins (see, e.g., Antos et al. (2008) *J. Am. Chem. Soc.* 130: 16338-16343);

4) Immobilization of proteins to biacore sensor chips using *Staphylococcus aureus* sortase A. This is important for the generation of biosensors (see, e.g., Clow et al. (2008) *Biotech. Letts.*);

5) Attachment of an NMR-invisible solubility enhancement tag using a sortase-mediated protein ligation method. Similar methods allow for the attachment of solubility tags to solubility limited proteins (see, e.g., Kobashigawa et al. (2009) *J. Biomol. NMR*, 43: 145-150);

6) Enzyme-mediated site-specific antibody-protein modification using a ZZ domain as a linker. These conjugates can be used to deliver proteins/small molecules using antibodies. Sakamoto et al. (2010) *Bioconjug. Chem.* 21: 2227-2233 observed ~65% ligation of antibody with protein target in 15 hours. It is believed the methods and compositions described herein improve these low rates and yields.

7) Observing selectively labeled domains by NMR. This allows users to selectively observe one domain of a multi-domain protein by NMR, simplifying spectral analysis (see, e.g., Refaei et al. (2011) *J. Biomol. NMR*, 49(1): 3-7); Freiburger et al. (2015) *J. Biomol. NMR*, 63: 1-8).

In various embodiments, the reagents contemplated herein include a protease recognition (cleavage) site disposed between the peptide that is to be ligated and the sortase. This permits the sortase to be subsequently removed from the ligated proteins by use of the corresponding protease.

A "protease recognition site" is a contiguous sequence of amino acids connected by peptide bonds that contains a pair of amino acids which is connected by a peptide bond that is hydrolyzed by a particular protease. Optionally, a protease recognition site can include one or more amino acids on either side of the peptide bond to be hydrolyzed, to which the catalytic site of the protease also binds (Schecter and Berger, (1967) *Biochem. Biophys. Res. Commun.* 27: 157-62), or the recognition site and cleavage site on the protease substrate can be two different sites that are separated by one or more (e.g., two to four) amino acids.

The specific sequence of amino acids in the protease recognition site typically depends on the catalytic mechanism of the protease, which is defined by the nature of the functional group at the protease's active site. For example, trypsin hydrolyzes peptide bonds whose carbonyl function is donated by either a lysine or an arginine residue, regardless of the length or amino acid sequence of the polypeptide chain. Factor Xa, however, recognizes the specific sequence Ile-Glu-Gly-Arg (SEQ ID NO:8) and hydrolyzes peptide bonds on the C-terminal side of the Arg. Various protease recognition sites include, but are not limited to protease recognition sites for proteases from the serine protease family, or for metalloproteases, or for a protease from the cysteine protease family, and/or the aspartic acid protease family, and/or the glutamic acid protease family. In certain embodiments serine proteases recognition sites include, but are not limited to recognition sites for chymotrypsin-like proteases, and/or subtilisin-like proteases, and/or alpha/beta hydrolases, and/or signal peptidases. In certain embodiments metalloprotease recognition sites include, but are not limited to recognition sites for metallocarboxypeptidases or metalloendopeptidases. Illustrative proteases and protease recognition sites are shown below in Table 1.

TABLE 1

Illustrative proteases and protease recognition sites (* indicates the peptide bond being hydrolyzed).

| Protease Family | Protease | Protease Recognition Sites |
|---|---|---|
| serine | factor Xa | Ile-Gly-Gly-Arg* (SEQ ID NO: 9) |
| serine | trypsin | Lys*, Arg* |
| serine | chymotrypsin | Tyr*, Phe*, Leu*, Ile*, Val*, Trp*, and His* at high pH |
| serine | thrombin | Arg* |
| serine and cysteine variants | peanut mottle polyvirus Nla protease | Glu1-Xaa-Xaa-TyrGln* (Ser/Gly) (SEQ ID NO: 10) |
| cysteine | papaine | Arg*, Lys*, Phe* |
| cysteine | bromelaine | Lys*, Ala*, Tyr*, Gly* |
| cysteine | cathepsin B | Arg*Arg, |
| cysteine | cathepsin L | Phe*Arg |
| aspartyl | HIV protease | Phe*Pro |
| aspartyl | S. cerevisiae yapsin 2 | Lys*, Arg* |
| aspartyl | cathepsin D | Phe*Phe Phe*Lys Leu*Phe Leu*Tyr |
| metallo- | thermolysin | *Tyr, *Phe, *Leu, *Ile, *Val, Trp, and *His |
| metallo- | peptidyl-Lys metalloendopeptidase | Xaa*Lys |
| metallo- | peptidyl-Asp metallodndopeptidase | Xaa* Asp Xaa* Glu Xaa* Cys |
| metallo- | coccolysin | *Leu, *Phe, *Tyr, *Ala |

TABLE 1 -continued

Illustrative proteases and protease recognition sites (* indicates the peptide bond being hydrolyzed).

| Protease Family | Protease | Protease Recognition Sites |
|---|---|---|
| metallo- | autolysin | Leu-Trp-Met*Arg-Phe-Ala |
| metallo- | gelatinase A (MMP-2) | Pro-Gln-Gly*Ile-Ala-Gly-Gln (SEQ ID NO: 11) |
| metallo- | human neutrophil collagenase (MMP-8) | Gly-Leu-Ser-Ser-Asn-Pro*IleGln-Pro (SEQ ID NO: 12) |

In certain embodiments the reagents described herein can further comprise one or more affinity tags to facilitate purification. Illustrative affinity tags include, but are not limited to avidin/streptavidin/biotin, polyhistidine (e.g., His6 (SEQ ID NO:4).

While the compositions and methods described herein utilize the Staphylococcus aureus SrtA sortase (or catalytic domain thereof) and the LPXTG (SEQ ID NO:2) the methods and compositions need not be so limited. In certain embodiments other sortases and recognition motifs are contemplated. Based on homology sortases thus far identified are typically grouped into four or five subgroups or classes (see, Table 2). Each subgroup, in addition to distinctions in sequence, can be distinguished from one another based on membrane topology, genome position, and preference for substrates with specific amino acids within the cell wall sorting signal pentapeptide motif (see, e.g., Comfort and Clubb (2004) Infect. Immun., 72: 2710-2722; Dramsi et al. (2005) Res. Microbiol. 156: 289-297). As indicated above, the prototypical sortase is sortase A, first identified in S. aureus. Sortase A appears to anchor a large number and broad range of surface proteins. The sortase A subgroup of enzymes also seems to share a preference for the LPXTG motif (SEQ ID NO:2, where X is any amino aid) cell wall sorting signal motif. A second subgroup of enzymes, sortase B, along with its substrate (IsdC in S. aureus), is encoded in an iron transport operon involved in heme-iron uptake. Enzymes belonging to the sortase B subgroup contain three amino acid segments not found in sortase A and recognize substrates containing an NPQTN (SEQ ID NO:13) motif rather than the canonical LPXTG (SEQ ID NO:24). A third class, designated sortase C or subfamily 3, contains a C-terminal hydrophobic domain (Id.). Subfamily 3 enzymes also share a preference for substrates containing the LPXTG (SEQ ID NO:24) cell wall sorting signal motif, often followed by a second G residue (i.e., LPXTGG, (SEQ ID NO:14). A fourth subgroup can be defined after alignment of sortase sequences. This has been designated as the sortase D subgroup (see, e.g., Dramsi et al. (2005) Res. Microbial. 156: 289-297) or subfamilies 4 and 5, as sortases in this subgroup can be distinguished based on the cell wall sorting signals of their associated substrates (Comfort and Clubb (2004) Infect. Immun., 72: 2710-2722). Sortases belonging to subfamily 4 are predicted to anchor proteins bearing the unique LPXTA(ST) (SEQ ID NO:15) motif (Id.). An alanine residue in the last position of the substrate motif suggests that the subfamily 4 enzymes fulfill a nonredundant role within the cell (Id.). Many high-G/C bacteria contain sortases belonging to subfamily 5, and most do not harbor sortase A. This subgroup of sortase enzymes shares substrate specificity for proteins containing an LAXTG (SEQ ID NO:16) motif (Id.).

TABLE 2

Sortase classifications.

| Sortase class (sub-family)a | Cleavage site[b] | Membrane anchor domain[c] | Bacterial taxa[d] |
|---|---|---|---|
| A (1) | LPkT-Ge* | N terminus | Bacillus, Listeria, Staphylococcus, Enterococcus, Lactobacillaceae, Streptococcaceae |
| B (2) | NPqt-nd* | N terminus | Bacillus, Listeria, Staphylococcus, Streptococcaceae, Clostridia |
| C (3) | 1PkT-GG | C terminus | Actinobacteria, Bacillus, Enterococcus, Leuconostocaceae, Streptococcaceae, Clostridia |
| D (4) | LPnT-At | N terminus | Bacillus |
| D (5) | LAeT-Ga | N terminus | Actinobacteria |

[a]Sortase subfamily and class assignments are based on sequence, membrane topology, genomic positioning, and preference for specific amino acids within the cell wall sorting signal pentapeptide motif region of their cognate substrates.
[b]Cell wall sorting signal pentapeptide motif. Uppercase letters represent amino acids that are absolutely conserved. Asterisks indicate that the cleavage site has been verified experimentally.

Accordingly in various embodiments, display systems that utilize any of these cell wall sorting sequences are contemplated for use in the methods and constructs described herein.

EXAMPLES

The following examples are offered to illustrate, but not to limit the claimed invention.

Example 1

Rapid Addition of Unlabeled Silent Solubility Tags to Proteins Using a New Substrate-Fused Sortase Reagent Many proteins can't be studied using solution NMR methods because they have limited solubility. To overcome this problem, recalcitrant proteins can be fused to a more soluble protein that functions as a solubility tag. However, signals arising from the solubility tag hinder data analysis because they increase spectral complexity. In this example, we describe a new method to rapidly and efficiently add a non-isotopically labeled SUMO solubility tag to an isotopically labeled protein. The method makes use of a newly developed SUMO-Sortase tagging reagent in which SUMO and the Sortase A (SrtA) enzyme are present within the same polypeptide. The SUMO-Sortase reagent rapidly attaches SUMO to any protein that contains the sequence LPXTG at its C-terminus. It modifies proteins up to 18-times faster than previously described approaches, and does not require active dialysis or centrifugation during the reaction to increase product yields. In addition, silently tagged proteins are readily purified using the well-established SUMO expression and purification system. The utility of the SUMO-Sortase tagging reagent is demonstrated using PhoP and green fluorescent proteins, which are ~90% modified with SUMO at room temperature within four hours. SrtA is widely used as a tool to construct bioconjugates. Significant rate enhancements in these procedures may also be achieved by fusing the sortase enzyme to its nucleophile substrate.

NMR spectroscopy is a powerful tool in which to study the structure and dynamics of proteins in solution (Cavanagh et al. (2010) Protein NMR Spectroscopy: Principles and Practice. Academic Press). However, in order to perform detailed studies, proteins must be soluble and stable in NMR compatible buffers at concentrations of ~250-500 μM or higher. Moreover, even higher protein concentrations are preferred as the signal-to-noise scales linearly with concentration. A significant problem limiting the study of many biologically interesting proteins is their limited solubility. Although a range of buffer conditions can be explored to improve protein solubility, many times these efforts prove unsuccessful. Fusing recalcitrant proteins to a more soluble domain (e.g. thioredoxin, maltose binding protein (MBP), protein G B1 domain (GB1), and glutathione-S-transferase domains (GST)) can dramatically improve overall solubility and are frequently used to facilitate expression and purification (di Guan et al. (1988) Gene, 67: 21-30; Smith and Johnson (1988) Gene, 67: 31-40; Huth et al. (1997) Protein Sci. 6: 2359-2364; LaVallie et al. (2000) Meth. Enzymol. 326: 322-340). Wagner and colleagues pioneered the use of protein "solubility tags" for NMR studies by demonstrating that the solubility and overall spectral quality of a poorly behaving protein can be improved by fusing it to GB1 (Zhou et al. (2001) J. Biomol. NMR, 20: 11-14; Zhou and Wagner (2009) J. Biomol. NMR, 46: 23-31). However, the NMR spectra of the GB1 fusion contained additional, unwanted signals from the solubility tag (GB1) that increased spectral complexity. To avoid this problem, newer "silent" solubility tagging methods have been developed in which the isotopically enriched protein of interest is first purified, and then ligated in vitro to an unlabeled, more soluble protein. Because the added solubility domain is not isotopically labeled, it is NMR "silent" and does not increase the spectral complexity (Zuger and Iwai (2005) Nat. Biotechnol. 23: 736-740; Kobashigawa et al. (2009) J. Biomol. NMR, 43: 145-150). Similar, in vitro ligation approaches are employed to segmentally isotope label multi-domain containing proteins, thereby reducing their spectral complexity (Yamazaki et al. (1998) J. Am. Chem. Soc. 120: 5591-5592; Muona et al. (2010) Nat. Protoc. 5: 574-587; Refaei et al. (2011) J. Biomol. NMR, 49: 3-7; Freiburger et al. (2015) J. Biomol. NMR, 63: 1-8).

Two approaches have been developed to attach silent solubility tags to proteins, intein trans-splicing and sortase catalyzed transpeptidation methods. In the intein trans-splicing method, split inteins self-associate to catalyze the splicing event (Yamazaki et al. (1998) J. Am. Chem. Soc. 120: 5591-5592; Xu et al. (1999) Proc. Natl. Acad. Sci. USA, 96: 388-393; Zuger and Iwai (2005) Nat. Biotechnol. 23: 736-740; Muona et al. (2010) Nat. Protoc. 5: 574-587). Silent tagging is performed in vitro, and requires both the target protein and solubility tag first be expressed and purified as a split-intein fusion. These fusion proteins are then joined via trans-splicing in which the split-intein components are eliminated. Although high yields are obtainable, reaction times of 1-2 days, and special protein reagents (the split-intein fusions) are required. A second approach uses the S. aureus sortase (SrtA) enzyme that joins via a peptide bond the protein of interest to the silent solubility tag. SrtA is a cysteine transpeptidase that catalyzes peptide bond formation between the threonine residue within the sequence LPXTG (SEQ ID NO:2, where X is any amino acid), and the amino group of a peptide that contains a penta-glycine ($Gly_5$ (SEQ ID NO:14)) sequence at its N-terminus (Mazmanian (1999) Science, 285:760-763; Perry et al. (2002) J. Biol. Chem. 277: 16241-16248; Spirig et al. (2011) Mol. Microbiol. 82:1044-1059). In elegant work by Kobashigawa and colleagues, SrtA was used to append a silent tag to the C-terminus of an isotopically labeled protein (Kobashigawa et al. (2009) *J. Biomol. NMR*, 43: 145-150). The reaction required three purified protein components: the unlabeled solubility tag containing an N-terminal pentaglycine sequence (Gly5-GB1 in their study), the isotopically enriched target protein containing a C-terminal LPXTG sequence, and the SrtA transpeptidase. Using this approach, 90% of the isotope labeled target protein was silently tagged with GB1 by performing the reaction for 3 days at room temperature. To improve yields the reaction was performed during dialysis to facilitate product removal. More recently, Sattler and colleagues demonstrated the utility of this approach for segmental labeling, and achieved faster modification rates by removing the product during the reaction by centrifugal concentration (Freiburger et al. (2015) *J. Biomol. NMR*, 63: 1-8).

Our objective was to create a more efficient and rapid solubility tagging method that satisfied the following criteria. First, proteins should be rapidly modified with the tag within a day, preferably in a process that can be conducted at lower temperatures to avoid protein aggregation and/or degradation of the isotopically labeled protein. Second, >90% of the labeled protein should be converted into the silently tagged protein product. This is critical as the target protein may be difficult to obtain and/or expensive to produce. Third, the tagging reaction should be a simple process that requires a minimum number of reagents, and should require only minor modification of the protein of interest. Finally, the procedure should be readily integrated into an established protein expression and purification scheme, enabling silently tagged proteins to be purified using conventional approaches.

Figure 2:
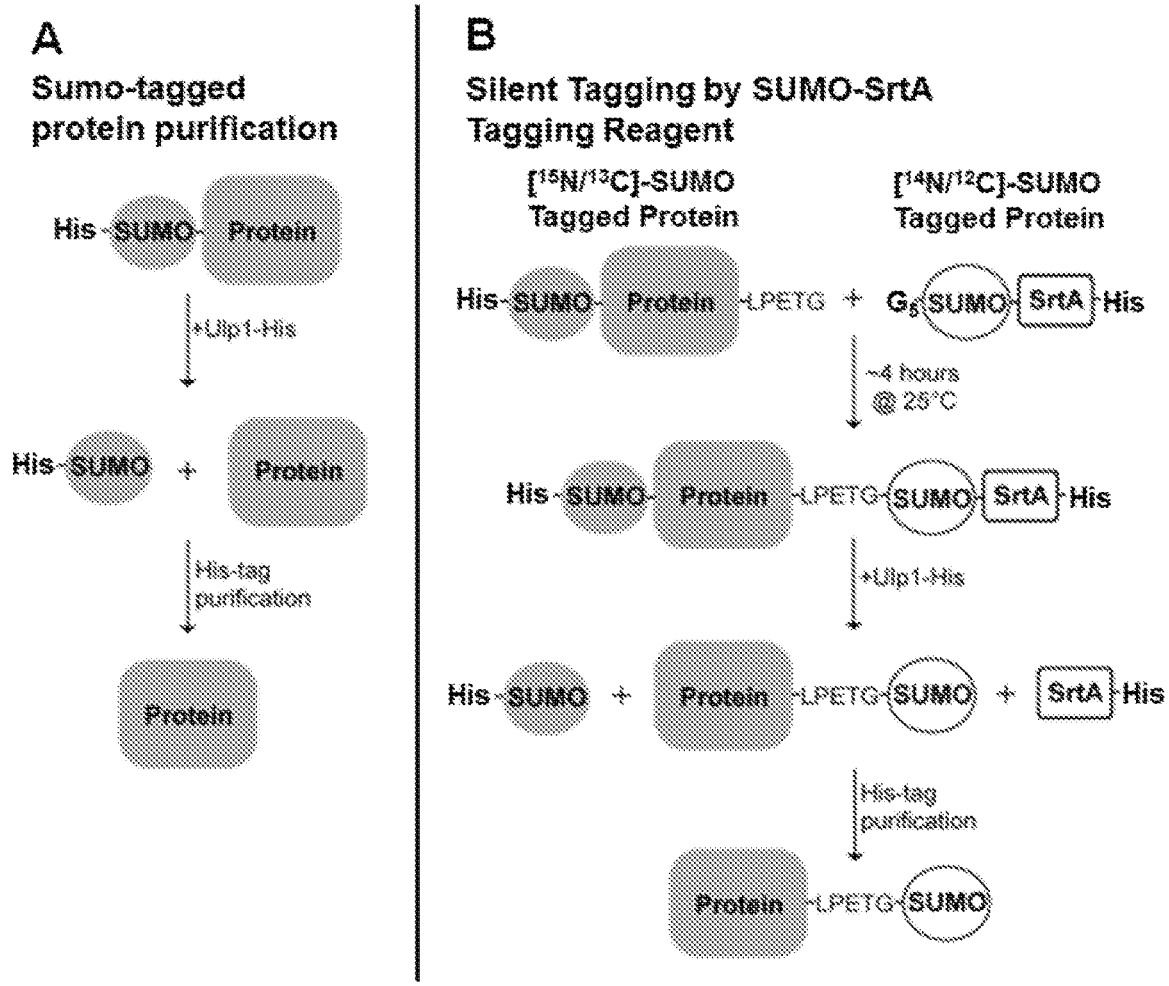
FIG. 2. Panel A: A schematic of a typical SUMO fusion purification. Panel B: A schematic of the Silent Tagging reaction by SUMO-SrtA. The target protein is expressed in isotopically enriched media producing a labeled fusion protein. If protein solubility is an issue one can opt for our system in which the target protein is expressed as a SUMO fusion protein with a C-terminal sortase, LPETG, recognition motif, aiding in overall expression and solubility. The unlabeled one-reagent SUMO-SrtA fusion tagging reagent will rapidly recognize the LPETG motif and cleave between the carbonyl of the threonine and glycine residues present in the motif. This reaction is resolved when the sortase Gly5 secondary substrate nucleophile, fused to the N-terminus of the unlabeled SUMO, enters the active site and the enzyme performs a transpeptidation reaction yielding the amino terminus of the penta-glycine motif appended to the LPET motif present in the target protein. This ligation mixture is then incubated with Ulp1, the SUMO protease, releasing the labeled SUMO solubility tag, and sortase enzyme from the ligation product. This allows for a rapid purification of the ligation product after cobalt affinity purification.

We developed a SUMO-tagging system that silently tags poorly soluble proteins with an unlabeled Small Ubiquitin-like Modifier (SUMO) protein. SUMO was chosen because of its low molecular weight (12 kDa), and because it has previously been shown to improve protein solubility (Malakhov et al. (2004 *J. Struct. Funct. Genomics*, 5: 75-86; Marblestone et al. (2006) *Protein Sci.* 15:182-189; Panavas et al. (2009) *Meth. Mol. Biol.* 497: 303-317; Peroutka Iii et al. (2011) *Meth. Mol. Biol.* 705: 15-30). Moreover, using SUMO as a solubility tag enables the new system to be integrated into the widely used, and commercially available, SUMO affinity tag purification (LifeSensors, Catalog no. 1001K, Malakhov et al. (2004 *J. Struct. Funct. Genomics*, 5: 75-86) or ThermoFisher (Catalog no. K300-01)). In the SUMO affinity tag purification procedure, proteins are produced as fusion with an N-terminal 6×His-SUMO affinity tag (FIG. 2, panel A). The 6×His-SUMO-Protein fusion is purified using standard immobilized metal affinity chromatography (IMAC) resin (e.g., $Ni^{2+}$ or $Co^{2+}$ columns). The 6×His-SUMO tag is then removed by adding the highly specific 6×His-Ulp1 protease, and the protein of interest is then purified by reapplying the mixture to the IMAC column. The protein of interest appears in the flow-through, while 6×His-Ulp1 protease and 6×His-SUMO are retained on the column. The SUMO-tagging system described here is readily integrated into this purification scheme because it makes use of 6×His-SUMO-Protein fusion, as well as the robust 6×His-Ulp1 protease. In our procedure, the isotopically enriched protein is expressed as a 6×His-SUMO-Protein fusion, an unlabeled SUMO tag is then added in a single step to the protein, and the desired Protein-SUMO fusion is generated using the conventional SUMO affinity tag purification scheme (FIG. 2, panel B). This approach is advantageous, as it simplifies procedures required to obtain the final product and because at all points in the process the protein remains fused to a solubility tag so as to minimize losses caused by aggregation.

The SUMO-tagging system is based on the SrtA-mediated approach developed by Kobashigawa and colleagues, but simplifies the process by creating a single SUMO-SrtA reagent that silently tags any protein containing the sequence LPXTG at its C-terminus (Kobashigawa et al. (2009) *J. Biomol. NMR*, 43: 145-150). Moreover, because SrtA and its SUMO substrate are located within the same polypeptide, the rate of modification ("tagging") is significantly increased (vide infra). The tagging reagent consists of a SUMO-SrtA fusion protein harboring five glycine residues at its N-terminus, and a histidine tag at its C-terminus (Gly5-SUMO-SrtA-6×His). Distinct from previous reported approaches, the ligation reaction requires only two components, the new tagging reagent and a purified protein that contains a C-terminal LPXTG sequence. To facilitate integration into SUMO affinity tag purification system, the protein to be tagged is produced as a 6×His-SUMO-Protein-LPETG fusion (FIG. 2, panel B). When the tagging reagent and fusion protein are incubated with one another, the reagent joins itself via a peptide bond to the C-terminal end of 6×His-SUMO-Protein-LPETG to create a 6×His-SUMO-Protein-LPET-Gly5-SUMO-SrtA-6×His ligation product. The ligation mixture is then incubated with 6×His-Ulp1 protease, releasing the N-terminal SUMO tag (6×His-SUMO), the SrtA enzyme (SrtA-6×His), and the desired tagged protein product (Protein-LPET-Gly5-SUMO). Because only the product lacks a histidine tag, it is purified by immobilized metal affinity chromatography (IMAC).

Figure 3:
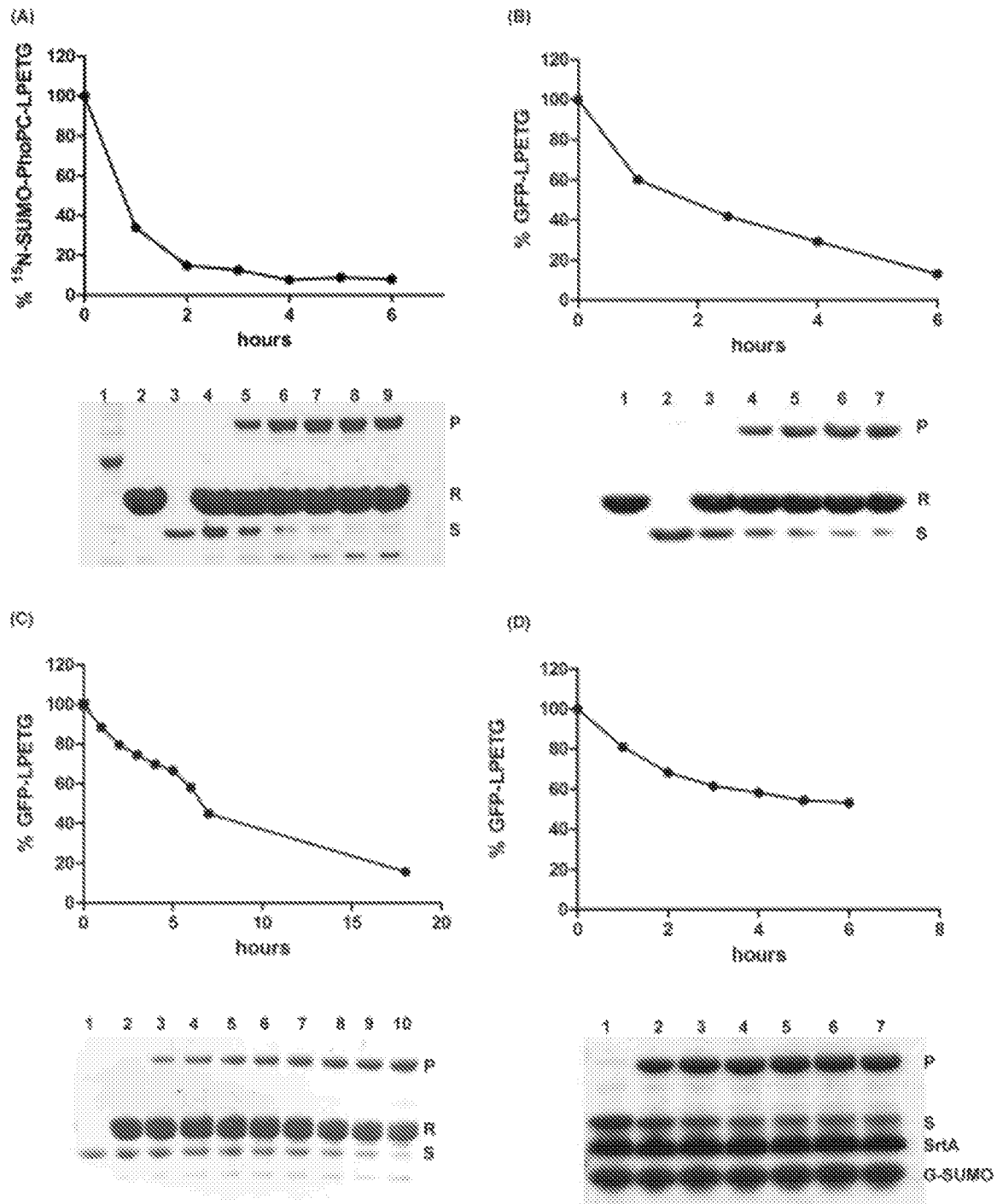
FIG. 3. Panel A: ImageJ analysis (top) of the SDS-PAGE results of conversion of $^{15}$N-SUMO-PhoPC-LPETG into $^{15}$N-SUMO-$^{14}$PhoPC-LPETG-N-SUMO. This reaction was carried out as a 5:1 mixture of the SUMO-SrtA single tagging reagent to N-SUMO-PhoPC-LPETG resulting in ~90% conversion to product in 4 hours at room temperature (25° C.). (bottom) Image of SDS-PAGE results indicate that the 5:1 incubation of the SUMO-SrtA ligation reagent with $^{15}$N-SUMO-PhoPC-LPETG results in the conversion of approximately 90% of the initial substrate into ligated product in approximately 4 hours at room temperature (25° C.). P, ligation product, R, SUMO-SrtA reagent, and S, SUMO-PhoPC-LPETG substrates. Lane 1. molecular weight ladder, lane 2, SUMO-SrtA tagging reagent, lane 3, $^{15}$N-SUMO-PhoPC-LPETG control, lane 4, 5:1 reagent:N-SUMO-PhoPC-LPETG ligation reaction 0 hour, lane 5, 1 hour, lane 6, 2 hours, lane 7, 3 hours, lane 8, 4 hours, lane 9, 6 hours. Panel B: representative ImageJ analysis (top) of the SDS-PAGE results (bottom) indicate that the 5:1 incubation of the SUMO-SrtA ligation reagent with GFP-LPETG results in the conversion of approximately 90% of the initial substrate into ligated product in approximately 5 hours at room temperature (25° C.). Lane 1, SUMO-SrtA tagging reagent, lane 2, GFP-LPETG, lane 3, 0 hour reaction, lane 4, 1 hour, lane 5, 2.5 hour, lane 6, 4 hours, lane 7, 6 hours. Panel C: ImageJ analysis (top) of the SDS-PAGE results (bottom) indicate that the 5:1 incubation of the SUMO-SrtA ligation reagent with GFP-LPETG results in the conversion of approximately 90% of the initial substrate into ligated product in approximately 18 hours at low temp (4° C.). Reactions done in the cold prevent degradation of the ligated product, tagging reagent, and target protein. Lane 1, GFP-LPETG control, lane 2, 5:1 reagent:GFP-LPETG ligation reaction 0 hour, lane 3, ligation reaction 1 hour, lane 4, 2 hours, lane 5, 3 hours, lane 6, 4 hours, lane 7, 5 hours, lane 8, 6 hours, lane 9, 7 hours, lane 10, 18 hours. Panel D: 3 component reaction does not have high yield or efficiency. ImageJ analysis (top) of the SDS-PAGE results of conversion of GFP-LPETG into ligation product. This reaction was carried out as a 5:1 mixture of the Gly$_5$-SUMO and SrtA-6×His to GFP-LPETG resulting in ~55% conversion to product in 6 hours at room temperature (25° C.). (bottom) Image of SDS-PAGE results of the 5:1 mixture of the Gly$_5$-SUMO and SrtA-6×His to GFP-LPETG (25° C.). Lane 1, reaction 0 hour, lane reaction 1 hour, lane 3, reaction 2 hours, lane 4, 3 hour, lane 5, 4 hours, lane 6, 5 hours, lane 7, 6 hours.

The utility of the SUMO-tagging system was initially demonstrated using the PhoP protein from *M. tuberculosis*. PhoP is a two-component response regulator that binds DNA through its C-terminal domain (PhoPC, residues 142-247 of PhoP) (Pathak et al. (2010) *J. Biol. Chem.* 285: 34309-34318; Macdonald et al. (2015) *J. Biomol. NMR*, 63: 111-117). PhoPC was chosen because the isolated domain exhibits limited solubility in NMR compatible buffers, and it requires high salt concentrations; PhoPC is initially soluble in buffer containing 50 mM sodium phosphate pH 6.5 and 300 mM NaCl, but the protein begins to aggregate and precipitate to below ~500 µM after ~24-48 hours. To tag PhoPC, a 6×His-SUMO-PhoPC-LPETG fusion protein was expressed from a commercially available pSUMO plasmid and purified by IMAC (FIG. 1, panel A). The protein was then incubated at 25° C. for varying amounts time with unlabeled tagging reagent (Gly5-SUMO-SrtA-6×His) at a 1:5 molar ratio of protein to reagent. As shown in FIG. 3, panel a, approximately 90% of PhoPC is converted into the ligated product within 4 hours. We also verified the robustness of the modification procedure using Green-fluorescent protein (GFP) containing the sequence LPETG at its C-terminus (GFP-LPETG). As shown in FIG. 3, panel b, when it is incubated with Gly5-SUMO-SrtA-6×His using similar reaction conditions, ~90% of GFP-LPETG is ligated to the tagging reagent within four hours. For some proteins, it may be desirable to add silent solubility tags using lower reaction temperatures to avoid protein aggregation and/or proteolysis. FIG. 3, panel c, shows that this can readily be accomplished using the reagent, as it only requires 18 hours to convert ~90% of GFP-LPETG into the tagged product when the reaction is performed at 4° C. (1:5 ratio molar ratio of protein to reagent).

Figure 4:
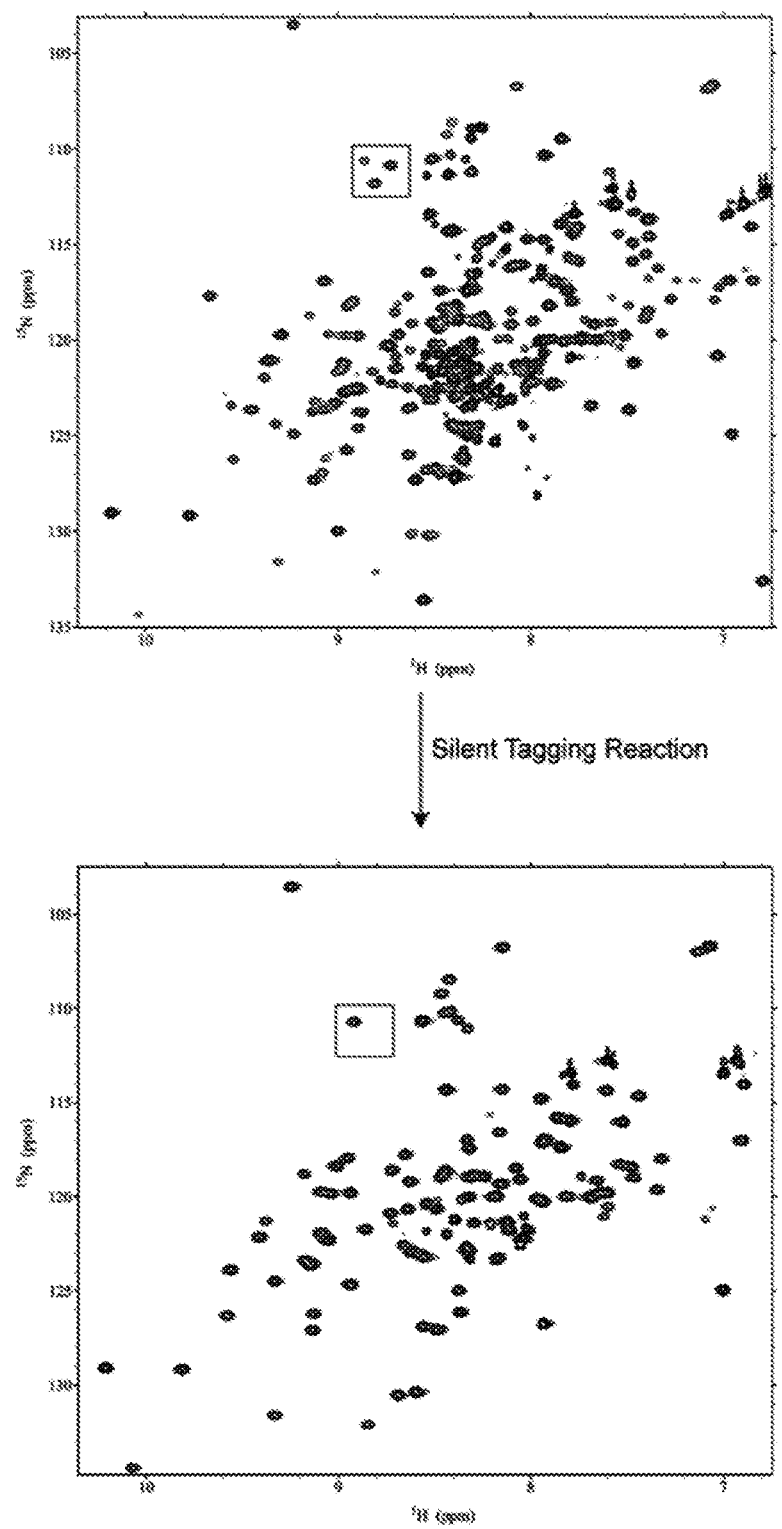
FIG. 4 shows HSQC of $^{15}$N-SUMO-PhoPC-LPETG prior to the SUMO-SrtA silent ligation reaction (top). HSQC of $^{15}$N-PhoPC-$^{14}$N-SUMO post SUMO-SrtA silent tagging reaction (bottom). The boxed regions shows regions where signals from the SUMO and PhoPC proteins originate and the removal of the SUMO signals post silent tagging reaction.

An attractive feature of the SUMO-tagging system is that the silently tagged protein product can readily be purified for NMR studies using the SUMO affinity tag protein purification system (FIG. 2). This was demonstrated by silently tagging U—[$^{15}$N]-PhoPC with unlabeled SUMO protein. The U—[$^{15}$N]-PhoPC protein was produced using the pSUMO vector as a His-SUMO-PhoPC-LPETG fusion and purified using IMAC (FIG. 2, panel A). The protein was then modified using the tagging reagent and processed by adding the Ulp1 protease, which selectively cleaves the peptide bond between residues in the Gly-Gly dipeptide sequence located at the C-terminus of SUMO. Ulp1 cleaves the ligation product at two sites, one cleavage event removes the labeled N-terminal SUMO domain, while the second cleavage removes SrtA. This releases the desired silently tagged U—[$^{15}$N]-PhoPC-[$^{14}$N]-SUMO protein, and the histidine tagged U—[$^{15}$N]-SUMO and SrtA proteins. Because U—[$^{15}$N]-PhoPC-[$^{14}$N]-SUMO is not histidine tagged, it is readily separated from the other reactants by IMAC; U—[$^{15}$N]-PhoPC-[$^{14}$N]-SUMO does not bind the IMAC column in the absence of imidazole, while the histidine tagged U—[$^{15}$N]-SUMO and SrtA reaction components bind the column. FIG. 4 shows that silent tagging eliminates spectral complexity caused by the solubility tag. The 1H-$^{15}$N HSQC spectrum of the U—[$^{15}$N]-SUMO-PhoPC-LPETG protein obtained prior to silent tagging contains signals arising from both PhoPC and the N-terminal SUMO domain, whereas only signals from PhoPC are observed in the silently tagged U—[$^{15}$N]-PhoPC-LPET-[$^{14}$N]-Gly5-SUMO protein (signals enclosed by a rectangle in FIG. 4 demonstrate the removal of SUMO resonances after the silent tagging reaction). Importantly, addition of the C-terminal silent SUMO tag to PhoPC enables protein concentrations in excess of 1 mM to be obtained, while lowering the amount NaCl that is required.

The SUMO-tagging reagent reported here silently tags proteins ~18 times faster than a previously described method that used the isolated SrtA enzyme; using our reagent ~90% reaction yields are obtained in 4 hours, whereas reaction times of three days are required when the isolated enzyme is employed (Kobashigawa et al. (2009) *J. Biomol. NMR*, 43: 145-150). The accelerated rate of modification presumably occurs because the effective concentration of the pentaglycine nucleophile near the enzyme active site in SrtA enzyme is increased because it is located within the same polypeptide. This is beneficial, as it overcomes SrtA's intrinsically weak affinity for the pentaglycine nucleophile (Km=140 μM) (Chen et al. (2011) *Proc. Natl. Acad. Sci. USA*, 108: 11399-11404). To directly explore the utility of fusing the enzyme to its nucleophile substrate, we performed a conventional three component SrtA-catalyzed reaction in which the reactants and SrtA were located on separate polypeptides. The isolated enzyme (SrtA-6×His), and Gly5-SUMO and GFP-LPETG substrates were mixed at a molar ratio of 5:5:1 at 25° C. (FIG. 3, panel d). In this three component reaction, only ~50% of the GFP-LPETG substrate is converted into product after 6 hours, a modification rate that is significantly slower than the rate obtained using the SUMO-tagging reagent that contains the nucleophile substrate fused to SrtA (compare FIGS. 3b and 3d). In the SUMO-SrtA reagent, the component proteins are connected by a ~12 amino acid linker that is presumably structurally disordered (Ilangovan et al. (2001) *Proc. Natl. Acad. Sci. USA*, 98: 6056-6061; Naik et al. (2006) *J. Biol. Chem.* 281: 1817-1826). Interestingly, this connector is critical for activity, as a deletion mutant of the reagent that removes the connector has greatly diminished activity (data not shown). This is presumably because in the reagent the connector segment is conformationally flexible, enabling the Gly5 nucleophile located at the N-terminal end of the SUMO domain in the SUMO-SrtA reagent to enter the active site of SrtA. Based on the established reaction mechanism of SrtA, the reagent can be expected to first cleave the LPXTG component of the substrate to form a thio-acyl bond to the target protein, which is then resolved by enhanced intramolecular nucleophilic attack by the Gly5 component of the reagent. In principle, even faster reaction rates may be obtainable by optimizing the connector segment to further increase the effective concentration of the Gly5 component of the reagent near the active site. Moreover, further optimization may be beneficial, since even though it is possible to produce 40 milligrams of pure Gly5-SUMO-SrtA-6×His reagent per liter of culture, the connector segment within the reagent is susceptible to proteolytic degradation necessitating a three-step purification procedure. However, it should be stressed, that once the reagent is purified it is stable for ~2-3 weeks when stored −20° C.

In this example we have described a new reagent that efficiently adds unlabeled SUMO solubility enhancement tags to proteins that are prone to aggregate at concentrations required for NMR studies. There are several advantages to our approach as compared to previously reported methods. First, proteins are tagged more rapidly, with ~90% of the target protein modified within ~4 hours, versus 2-3 days when other methods are used. Additionally, we have demonstrated that efficient tagging can be achieved at lower temperatures (4° C.). Second, it requires minimal modification of the target protein as only the LPXTG sequence needs to be added, unlike other methods that require the production of split intein protein fusions. Third, the new method is designed to be used with the well-established SUMO expression and purification system (FIG. 2). This facilitates purification of the tagged product and enables the potential utility of solubility tagging to be easily assessed without having to modify the protein of interest. This is because the NMR spectra of the 6×His-SUMO-Protein intermediate that is produced during the standard SUMO expression and purification procedure are expected to be similar to the spectra of the final silently tagged protein, albeit the spectra of the intermediate will contain additional signals from SUMO. Thus, if the spectra of 6×His-SUMO-Protein intermediate are of good quality it is worthwhile to perform the silent tagging reaction. Finally, as compared to previously described methods that use SrtA, the new method requires fewer protein components in the reaction (two instead of three), and rapid modification is obtained without the need for dialysis or centrifugation during the ligation reaction (Kobashigawa et al. (2009) *J. Biomol. NMR*, 43: 145-150; Refaei et al. (2011) *J. Biomol. NMR*, 49: 3-7; Freiburger et al. (2015) *J. Biomol. NMR*, 63: 1-8). In addition to silent tagging, SrtA has been successfully used to label cells, add proteins to solid supports, and to generate antibody conjugates, nucleic acid-protein fusions, and PEGylation/Lipidated proteins (Parthasarathy et al. (2007) *Bioconjug. Chem.* 18: 469-476; Chan et al. (2007) *PLoS One* 2: e1164; Pritz et al. (2007) *J. Org. Chem.* 72: 3909-3912; Antos et al. (2008) *J. Am. Chem. Soc.* 130: 16338-16343; Sakamoto et al. (2010) *Bioconjug. Chem.* 21: 2227-22233; Levary et al. (2011) *PLoS One*, 6: e18342). In principle, the approach described here could be used to significantly increase the rate and extent of modifications in these procedures by fusing the nucleophile substrate to the sortase enzyme.

Methods

Preparation of the SUMO-SrtA Tagging Reagent and Substrates.

The SUMO-tagging reagent (Gly5-SUMO-SrtA-6×His) used in this study contained SUMO connected to the N-terminus of residues 59-206 of SrtA. Appended to the N- and C-terminus of this polypeptide was the sequence GGGGG (Gly5) (SEQ ID NO:1) and HHHHHH (6×His) (SEQ ID NO:4). The plasmid overexpressing the SUMO-SrtA tagging reagent was generated by traditional restriction digest cloning. This was accomplished by ligating the SrtA gene insert into the pSUMO vector (LifeSensors) using BamHI and XhoI restriction enzymes and using the Quikchange mutagenesis reaction to add N-terminal Gly5 sequence (Agilent). The GFP and PhoPC substrates that were modified by the SUMO-SrtA tagging reagent were expressed from the pSUMO plasmid and contained the amino acid sequence LPETGGEST (SEQ ID NO:17) at their C-termini introduced using the Quikchange mutagenesis method.

All proteins were expressed in appropriately transformed Escherichia coli (E. coli) BL21 (DE3) cells. The unlabeled U—[$^{14}$N]-Gly5-SUMO-SrtA tagging reagent cultures were grown at 37° C. to an OD600 of 0.6 before induction with isopropyl b-D-thiogalactoside (IPTG) (Goldbio) to a final concentration of 1 mM in LB media. Induction proceeded at 18° C. overnight before harvesting the cells by centrifugation at 7000 g for 10 min at 4° C. The cell pellet was then resuspended in lysis buffer consisting of: 50 mM Tris-HCl, 300 mM NaCl (pH 8.0) containing protease inhibitor cocktail (Calbiochem) and phenylmethanesulfonyl fluoride (PMSF) (Sigma). Cells were lysed by sonication and centrifuged at 15,000 g for 50 min at 4° C. The supernatant was then incubated with 6.0 mL of pre-equilibrated Co2+ resin (Thermo) for 10 min at 4° C. on a rotisserie before being transferred to a gravity column. The resin was then washed with 100 mL lysis buffer, and the protein was finally eluted by adding lysis buffer containing 150 mM imidazole. Fractions containing the Gly5-SUMO-SrtA A59 tagging reagent were then buffer exchanged via concentrator (Amicon) into 50 mM MES pH6.0 buffer for HiTrap SP HP ion exchange chromatography (GE Healthcare). The Gly5-SUMO-SrtA reagent was eluted from the 5 mL SP HP column by a linear gradient over 40 mins into 50 mM MES pH6.0, 1 M NaCl. A final gel-filtration (Superdex 75 pg, GE Healthcare) step is carried out to remove any further contaminants and buffer exchange into the ligation reaction buffer, 50 mM Tris-HCl pH 7.5, 150 mM NaCl, 10 mM CaCl2. The SUMO-GFP-LPETG and SUMO-PhoPC-LPETG proteins were expressed and purified in a similar fashion. However they did not require further downstream ion exchange or gel-filtration chromatography, a one-step Co2+ affinity purification yielded highly pure protein. The proteins were buffer exchanged into ligation reaction buffer, 50 mM Tris-HCl pH 7.5, 150 mM NaCl, 10 mM CaCl2 by dialysis.

Ligation Reactions:

All ligation reactions were performed in 1.7 mL Eppendorf tubes rotating at either room temperature (25° C.) or in the cold at 4° C. Reactions were performed in 50 mM Tris-HCl pH 7.5, 150 mM NaCl, 10 mM CaCl2 buffer and contained 5:1 molar ratio of the SUMO-SrtA tagging reagent to labelled target protein. Typically, proteins concentrations of ~125 pM and ~25 μM were used for SUMO-SrtA and its substrate protein, respectively. The progress of the reactions was followed by sodium dodecyl sulfate-Polyacrylamide gel electrophoresis (SDS-PAGE) and the band intensity quantified densitometry using the program ImageJ (NIH). Post-ligation purification was carried out within 24 hours of the reaction. Briefly, the ligated product of the reaction, U—[$^{15}$N] SUMO-Protein-LPET-[$^{14}$N]-Gly5-SUMO-SrtA, is dialyzed into 50 mM Tris-HCl pH 8.0, 150 mM NaCl buffer and Ulp1 protease was added at a 25:1 molar ratio. After incubation overnight at 4° C., the final ligated product was obtained by application to a Co$^{2+}$ affinity column. It is important to note that in the absence of a nucleophile substrate the sortase enzyme functions as a protease and can cleave the final protein product (U—[$^{15}$N] SUMO-Protein-LPET-[$^{14}$N]-Gly5-SUMO-SrtA) unless the enzyme is removed. For our reactions we found that the product was stable for 24-36 hours in the presence of SUMO-tagging reagent (Gly5-SUMO-SrtA-6×His) and that proteolysis of the substrate was not a problem if the ligated product was immediately processed by the addition of Ulp1 protease and IMAC chromatography. However, it is important to note that the ligated product can readily be stabilized by adding a sortase inhibitor (p-hydroxymecuribenzoic acid, Sigma) after the ligation reaction is complete, as this small molecule inhibits the activity of the sortase enzyme but does not affect the activity of Ulp1 protease.

NMR Data Acquisition and Processing $^{1}$H-$^{15}$N-HSQC NMR experiments were performed at 298 K on a Bruker Avance HD 600-MHz spectrometer and Bruker Avance II 500-MHz spectrometer equipped with triple resonance cryogenic probes. NMR spectra were processed using NMRPipe (Delaglio et al. (1995) J. Biomol. NMR, 6: 277-293).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A reagent for ligating a desired polypeptide to a target moiety having a linking peptide attached thereto where the linking peptide comprises an LPXTG (SEQ ID NO: 2) amino acid motif in the carboxyl terminal of the linking peptide, said reagent comprising:
a polypeptide comprising an amino terminal polyglycine sequence comprising at least three contiguous Gly residues sequence followed by said desired polypeptide sequence followed by a sequence comprising the catalytic domain of a Sortase A enzyme.

2. The reagent of claim 1, wherein said polyglycine sequence comprises or consists of at least four contiguous Gly residues.

3. The reagent of claim 1, wherein said polyglycine sequence comprises or consists of at least five contiguous Gly residues.

4. The reagent of claim 1, wherein said reagent catalyzes a transpeptidation reaction substantially more rapidly and/or substantially more completely than a transpeptidation reaction performed using a sortase without an attached amino terminal pentaglycine.

5. The reagent according to of claim 1, wherein a protease cleavage site is disposed between said desired polypeptide and said Sortase A enzyme.

6. The reagent of claim 5, wherein said protease cleavage site comprises a protease site recognized by a protease selected from the group consisting of a serine protease, a cysteine or cysteine-like protease, and a metalloprotease.

7. The reagent of claim 5, wherein said protease cleavage site comprises a protease site recognized by Ulp-1.

8. The reagent of claim 1, wherein said reagent further comprises a carboxyl terminal affinity tag.

9. The reagent of claim 8, wherein said affinity tag comprises a poly histidine tag.

10. The reagent of claim 8, wherein said affinity tag comprises a His6 (SEQ ID NO:4) tag.

11. The reagent of claim 1, wherein said catalytic domain of a sortase A enzyme comprise a catalytic domain of a *Staphylococcus aureus* sortase A enzyme.

12. The reagent of claim 1, wherein said wherein said desired protein ranges in length from about 5 up to about 200 amino acids.

13. The reagent of claim 1, wherein said desired protein comprises SUMO.

14. The reagent of claim 1, wherein the amino acid sequence of said linking peptide comprises an amino acid sequence selected from the group consisting of LPETG (SEQ ID NO:18), LPATG (SEQ ID NO:19), LPKTG (SEQ ID NO:20), LPTTG (SEQ ID NO:21), LPSTG (SEQ ID NO:22), LPLTG (SEQ ID NO:23), and LPYTG (SEQ ID NO:24).

15. The reagent of claim 14, wherein the amino acid sequence of said linking peptide consists of an amino acid sequence selected from the group consisting of LPETG (SEQ ID NO:18), LPATG (SEQ ID NO:19), LPKTG (SEQ ID NO:20), LPTTG (SEQ ID NO:21), LPSTG (SEQ ID NO:22), LPLTG (SEQ ID NO:23), and LPYTG (SEQ ID NO:24).

16. The reagent of claim 14, wherein the amino acid sequence of said linking peptide comprises the amino acid sequence LPETG (SEQ ID NO:18).

17. The reagent of claim 16, wherein the amino acid sequence of said linking peptide consists of the amino acid sequence LPETG (SEQ ID NO:18).

* * * * *

SEQUENCE LISTING

<160> NUMBER OF SEQ ID NOS: 24

<210> SEQ ID NO 1
<211> LENGTH: 5
<212> TYPE: PRT
<213> ORGANISM: Artificial
<220> FEATURE:
<223> OTHER INFORMATION: Polyglycine peptide

<400> SEQUENCE: 1

Gly Gly Gly Gly Gly
1               5

<210> SEQ ID NO 2
<211> LENGTH: 5
<212> TYPE: PRT
<213> ORGANISM: Artificial
<220> FEATURE:
<223> OTHER INFORMATION: Sortase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Leu Pro Xaa Thr Gly
1               5

<210> SEQ ID NO 3
<211> LENGTH: 4
<212> TYPE: PRT
<213> ORGANISM: Artificial
<220> FEATURE:
<223> OTHER INFORMATION: Polyglycine peptide

<400> SEQUENCE: 3

Gly Gly Gly Gly
1

<210> SEQ ID NO 4
<211> LENGTH: 6
<212> TYPE: PRT
<213> ORGANISM: Artificial
<220> FEATURE:
<223> OTHER INFORMATION: Polyhistidine affinity tag

<400> SEQUENCE: 4

His His His His His His
1               5

<210> SEQ ID NO 5
<211> LENGTH: 8
<212> TYPE: PRT
<213> ORGANISM: Artificial
<220> FEATURE:
<223> OTHER INFORMATION: Epitope tag

<400> SEQUENCE: 5

Asp Tyr Lys Asp Asp Asp Asp Lys
1               5

<210> SEQ ID NO 6
<211> LENGTH: 5
<212> TYPE: PRT
<213> ORGANISM: Artificial
<220> FEATURE:
<223> OTHER INFORMATION: Peptide linker

<400> SEQUENCE: 6

Gly Gly Gly Gly Ser
1               5

<210> SEQ ID NO 7
<211> LENGTH: 15
<212> TYPE: PRT
<213> ORGANISM: Artificial
<220> FEATURE:
<223> OTHER INFORMATION: Peptide linker

<400> SEQUENCE: 7

```
Gly Gly Gly Gly Ser Gly Gly Gly Ser Gly Gly Gly Ser
1               5                   10                  15

<210> SEQ ID NO 8
<211> LENGTH: 4
<212> TYPE: PRT
<213> ORGANISM: Artificial
<220> FEATURE:
<223> OTHER INFORMATION: Protease recognition motif

<400> SEQUENCE: 8

Ile Glu Gly Arg
1

<210> SEQ ID NO 9
<211> LENGTH: 4
<212> TYPE: PRT
<213> ORGANISM: Artificial
<220> FEATURE:
<223> OTHER INFORMATION: Protease recognition motif

<400> SEQUENCE: 9

Ile Gly Gly Arg
1

<210> SEQ ID NO 10
<211> LENGTH: 6
<212> TYPE: PRT
<213> ORGANISM: Artificial
<220> FEATURE:
<223> OTHER INFORMATION: Protease recognition motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 10

Glu Xaa Xaa Tyr Gln Xaa
1               5

<210> SEQ ID NO 11
<211> LENGTH: 7
<212> TYPE: PRT
<213> ORGANISM: Artificial
<220> FEATURE:
<223> OTHER INFORMATION: Protease recognition motif

<400> SEQUENCE: 11

Pro Gln Gly Ile Ala Gly Gln
1               5

<210> SEQ ID NO 12
<211> LENGTH: 9
<212> TYPE: PRT
<213> ORGANISM: Artificial
<220> FEATURE:
<223> OTHER INFORMATION: Sortase recognition motif

<400> SEQUENCE: 12

Gly Leu Ser Ser Asn Pro Ile Gln Pro
1               5

<210> SEQ ID NO 13
```

```
<211> LENGTH: 5
<212> TYPE: PRT
<213> ORGANISM: Artificial
<220> FEATURE:
<223> OTHER INFORMATION: Sortase recognition motif

<400> SEQUENCE: 13

Asn Pro Gln Thr Asn
1               5

<210> SEQ ID NO 14
<211> LENGTH: 6
<212> TYPE: PRT
<213> ORGANISM: Artificial
<220> FEATURE:
<223> OTHER INFORMATION: Sortase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 14

Leu Pro Xaa Thr Gly Gly
1               5

<210> SEQ ID NO 15
<211> LENGTH: 6
<212> TYPE: PRT
<213> ORGANISM: Artificial
<220> FEATURE:
<223> OTHER INFORMATION: Sortase recognition motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 15

Leu Pro Xaa Thr Ala Xaa
1               5

<210> SEQ ID NO 16
<211> LENGTH: 5
<212> TYPE: PRT
<213> ORGANISM: Artificial
<220> FEATURE:
<223> OTHER INFORMATION: Sortase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 16

Leu Ala Xaa Thr Gly
1               5

<210> SEQ ID NO 17
<211> LENGTH: 9
<212> TYPE: PRT
<213> ORGANISM: Artificial
<220> FEATURE:
<223> OTHER INFORMATION: SUMO sequence

<400> SEQUENCE: 17

Leu Pro Glu Thr Gly Gly Glu Ser Thr
1               5
```

```
<210> SEQ ID NO 18
<211> LENGTH: 5
<212> TYPE: PRT
<213> ORGANISM: Artificial
<220> FEATURE:
<223> OTHER INFORMATION: Peptide linker

<400> SEQUENCE: 18

Leu Pro Glu Thr Gly
1               5

<210> SEQ ID NO 19
<211> LENGTH: 5
<212> TYPE: PRT
<213> ORGANISM: Artificial
<220> FEATURE:
<223> OTHER INFORMATION: Peptide linker

<400> SEQUENCE: 19

Leu Pro Ala Thr Gly
1               5

<210> SEQ ID NO 20
<211> LENGTH: 5
<212> TYPE: PRT
<213> ORGANISM: Artificial
<220> FEATURE:
<223> OTHER INFORMATION: Peptide linker

<400> SEQUENCE: 20

Leu Pro Lys Thr Gly
1               5

<210> SEQ ID NO 21
<211> LENGTH: 5
<212> TYPE: PRT
<213> ORGANISM: Artificial
<220> FEATURE:
<223> OTHER INFORMATION: Peptide linker

<400> SEQUENCE: 21

Leu Pro Thr Thr Gly
1               5

<210> SEQ ID NO 22
<211> LENGTH: 5
<212> TYPE: PRT
<213> ORGANISM: Artificial
<220> FEATURE:
<223> OTHER INFORMATION: Peptide linker

<400> SEQUENCE: 22

Leu Pro Ser Thr Gly
1               5

<210> SEQ ID NO 23
<211> LENGTH: 5
<212> TYPE: PRT
<213> ORGANISM: Artificial
<220> FEATURE:
<223> OTHER INFORMATION: Peptide linker

<400> SEQUENCE: 23

Leu Pro Leu Thr Gly
1               5
```

```
<210> SEQ ID NO 24
<211> LENGTH: 5
<212> TYPE: PRT
<213> ORGANISM: Artificial
<220> FEATURE:
<223> OTHER INFORMATION: Peptide linker

<400> SEQUENCE: 24

Leu Pro Tyr Thr Gly
1               5
```